(12) United States Patent
Lacey

(10) Patent No.: US 10,485,835 B2
(45) Date of Patent: Nov. 26, 2019

(54) HAND WRAP INCLUDING EUCALYPTUS OIL

(71) Applicant: Drum Nerd, La Grange, IL (US)

(72) Inventor: Ryan Lacey, La Grange, IL (US)

(73) Assignee: Drum Nerd, La Grange, IL (US)

( * ) Notice: Subject to any disclaimer, the term of this patent is extended or adjusted under 35 U.S.C. 154(b) by 0 days.

(21) Appl. No.: 15/817,498

(22) Filed: Nov. 20, 2017

(65) Prior Publication Data

US 2018/0140652 A1    May 24, 2018

Related U.S. Application Data

(60) Provisional application No. 62/423,953, filed on Nov. 18, 2016.

(51) Int. Cl.
*A61K 36/61* (2006.01)
*A41D 13/08* (2006.01)

(52) U.S. Cl.
CPC ............ *A61K 36/61* (2013.01); *A41D 13/081* (2013.01); *A41D 13/087* (2013.01); *A41D 2400/32* (2013.01)

(58) Field of Classification Search
CPC .............................. A41D 13/081; A61K 36/61
See application file for complete search history.

(56) References Cited

U.S. PATENT DOCUMENTS

| | | | | |
|---|---|---|---|---|
| 6,074,413 A * | 6/2000 | Davis | ........................ | A61F 7/03 607/108 |
| 6,576,004 B2 * | 6/2003 | Johnston | ................... | A61F 7/02 607/114 |
| 6,666,747 B1 * | 12/2003 | Buntz | .................... | A41C 3/065 424/400 |
| 8,282,607 B2 * | 10/2012 | Smith | .................. | A61K 9/1272 206/484.2 |
| 9,675,727 B2 * | 6/2017 | Jacques | ................ | A61K 9/7023 |
| 2009/0204092 A1 * | 8/2009 | Loyd | ..................... | A61F 13/472 604/385.03 |
| 2009/0287280 A1 * | 11/2009 | Wong | ...................... | A61F 7/034 607/96 |
| 2014/0352090 A1 * | 12/2014 | Schuchter | ............ | A61K 8/0208 15/104.93 |
| 2016/0128950 A1 * | 5/2016 | Mitroo | ................... | A61K 36/79 604/290 |
| 2016/0338941 A1 * | 11/2016 | DeMille | ................. | A61K 8/922 |

OTHER PUBLICATIONS

Vegan Street DIY Chemical-Free Dryer Sheets. http://www.veganstreet.com/diydryersheets.html. Available via Wayback machine at https://web.archive.org/web/20150523064534/http://www.veganstreet.com/diydryersheets.html at least as of May 23, 2015. (Year: 2015).*

* cited by examiner

Primary Examiner — Kristen Matter
(74) Attorney, Agent, or Firm — Stinson LLP

(57) ABSTRACT

Hand wrap includes *eucalyptus* oil absorbed in a roll of fabric material.

1 Claim, 4 Drawing Sheets

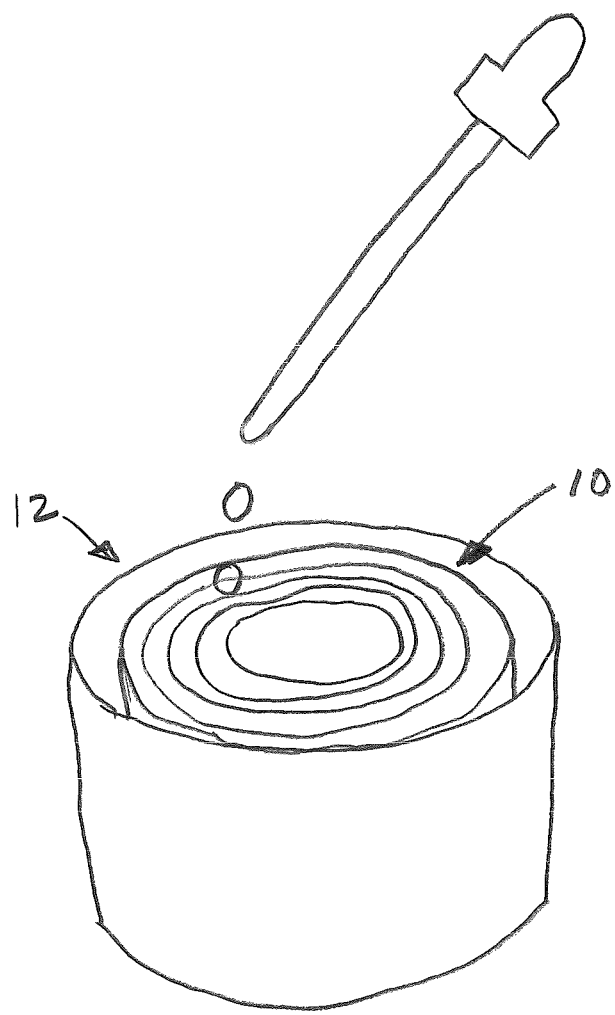

HAND WRAP INCLUDING EUCALYPTUS OIL

FIELD OF THE DISCLOSURE

The present disclosure generally relates to wrap including *eucalyptus* oil for protecting a hand of a user during an activity.

BACKGROUND

Drummers, particularly hand drummers, use tape on their fingers to prevent injuries to their hands during playing. People may wrap their hands or fingers while during other activities to also prevent injuries.

SUMMARY

In one aspect, hand wrap generally comprises a roll of fabric material; and *eucalyptus* oil absorbed in the roll of fabric material.

BRIEF DESCRIPTION OF THE DRAWINGS

FIG. 4 illustrates an exemplary process of infusing wrap with *eucalyptus* oil.

Corresponding reference characters indicate corresponding parts throughout the drawings.

DETAILED DESCRIPTION OF THE DISCLOSURE

Figure 1:
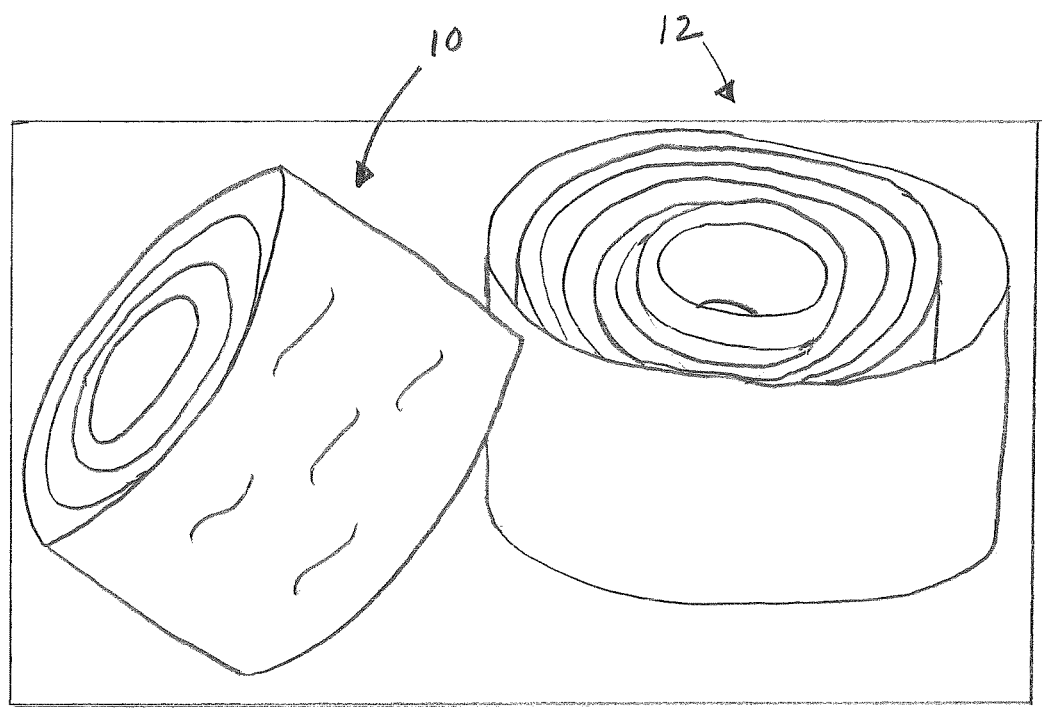
FIG. 1 is a perspective of a roll of wrap including *eucalyptus* oil and a container for the tape.

Referring to FIG. 1 of the drawings, one embodiment of a roll of wrap including *eucalyptus* oil is indicated at reference numeral 10. The wrap is suitable for being applied to a hand of a user, which may include one or more finger. Preferably, the wrap is applied directly to skin of the user's hand. The wrap may comprise 100% cotton fabric or other suitable fabric or material for absorbing *eucalyptus* oil. In one example, the wrap comprises adhesive tape having an inner side including an adhesive material suitable for adhering temporarily to skin of the user, and an outer side preferably free from adhesive. The adhesive wrap or tape may comprise 100% cotton, zinc oxide athletic tape. Such athletic tape may be purchased from Mueller Sports Medicine, Inc. It is understood that the adhesive wrap may comprise other materials without necessarily departing from the scope of the invention, so long as the tape comprises material suitable for absorbing *eucalyptus* oil. In another example, the inner and outer sides of the wrap may be free from adhesive. In yet another example, one or both of the inner and outer sides may include adhesive or other material.

*Eucalyptus* oil is absorbed (i.e., infused) in the wrap. In one example, the *eucalyptus* oil is absorbed in cotton or other absorbing material of the wrap. In one embodiment, the *eucalyptus* oil is absorbed in the wrap before rolling the wrap into a roll, as illustrated. In another embodiment, the *eucalyptus* oil is absorbed in the wrap after rolling the wrap into the roll. One example of making the roll of wrap including *eucalyptus* oil is described in the below example.

Figure 2:
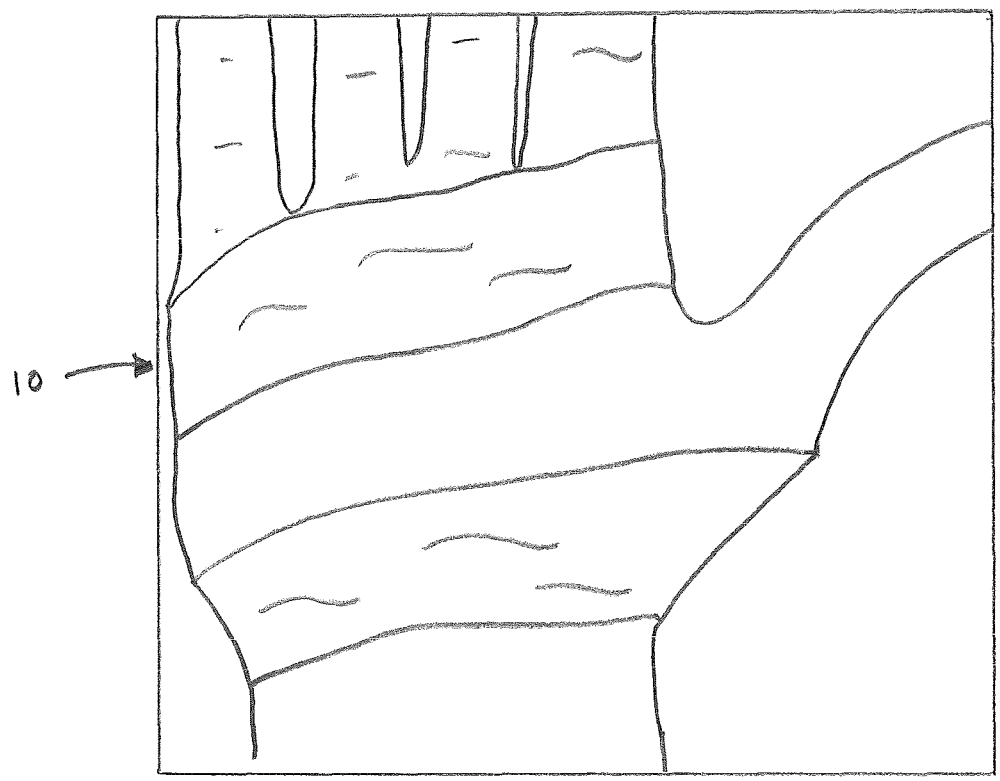
FIG. 2 is a photo of wrap applied to a hand of a user.
Figure 3:
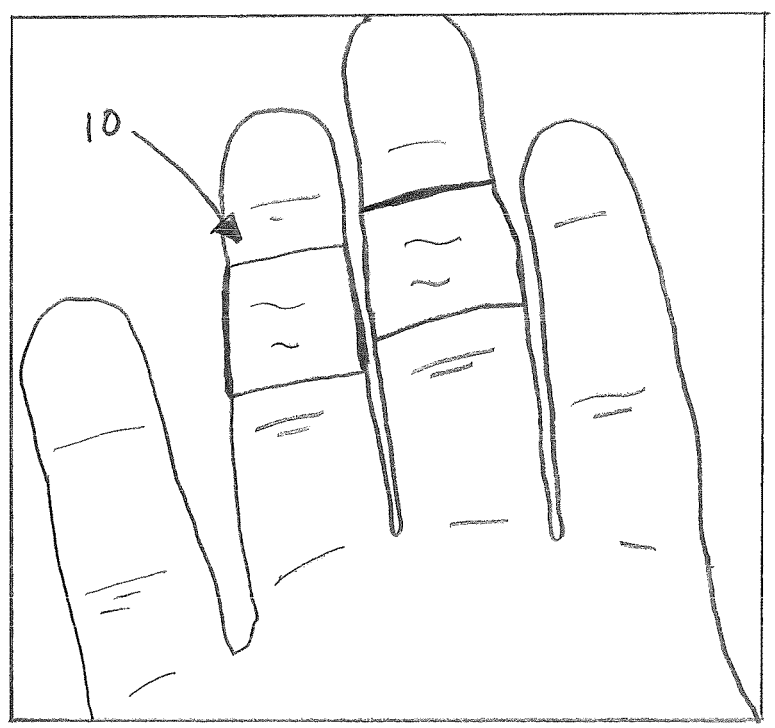
FIG. 3 is a photo of wrap applied to fingers of a hand of a user.

In one example of using, the wrap is applied to the user's hands. The wrap may be wrapped around the user's hands and/or fingers in any suitable way for protecting the user's hands and/or fingers during an activity, such as shown in FIGS. 2 and 3. Such an activity includes, but is not limited to, drumming (e.g., hand drumming), rowing, boxing, martial arts, golf, baseball, and other activities using one's hands. After applying the wrap to the user's hands, chemical compounds contained in the *eucalyptus* oil are applied to the user's hands via the wrap and absorbed into the skin of the user. It is believed that the chemical compounds in the *eucalyptus* oil provide anti-inflammatory and pain relief to the user's hands, among other benefits. For example, the chemical compound eucalyptol is released from the wrap and absorbed by the user's skin. Other chemical compounds within the *eucalyptus* oil may also be applied to the user's skin to provide other benefits.

EXAMPLE

Provide a roll 10 of Mueller M athletic tape (100% cotton backcloth, zinc oxide trainer's tape). The roll of tape is 1.5 inches×10 yards. Tape weight is 2.4 ounces.

Provide container 12 for the tape.

Provide 100% *eucalyptus* oil. Brand of *eucalyptus* oil is NOW® essential oils.

Perform the following steps, referring to FIG. 4:
1. Drip 7 drops of *eucalyptus* oil onto the bottom of the inside of the empty container using the dropper from the NOW® *eucalyptus* oil product;
2. Spin the top side of tape roll around in the oil;
3. Take the tape out of the container;
4. Apply 3-4 additional drops of oil directly to the top of the tape roll outside of the container (on the side already infused) and rub it in with finger;
4. Drip 7 more drops of *eucalyptus* oil onto the bottom of the inside of the empty container;
5. Spin the bottom side of tape roll around in the oil on the bottom inside of the container so both sides of the tape are infused; and
6. Immediately cap and seal the container with a heat gun blower and shrink bands.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of making a hand wrap product, the method comprising:

providing a roll of fabric material, the roll having a top side, a bottom side, an inner side, and an outer side, at least one of the inner or outer side comprising an adhesive configured to secure the hand wrap product to a hand of a user;

adding *eucalyptus* oil to an interior bottom of a container;

placing the top side of the roll onto the interior bottom of the container such that the top side of the roll becomes infused with the *eucalyptus* oil;

removing the roll from the container after the roll absorbs the *eucalyptus* oil;
applying drops of *eucalyptus* oil directly to the top side of the roll infused with the *eucalyptus* oil;
adding additional *eucalyptus* oil to the interior bottom of the container;
placing the bottom side of the roll onto the interior bottom of the container such that the bottom side of the roll becomes infused with the additional *eucalyptus* oil;
capping the container with the roll inside of the container; and
sealing the container with shrink wrap.

\* \* \* \* \*